Figure 1:
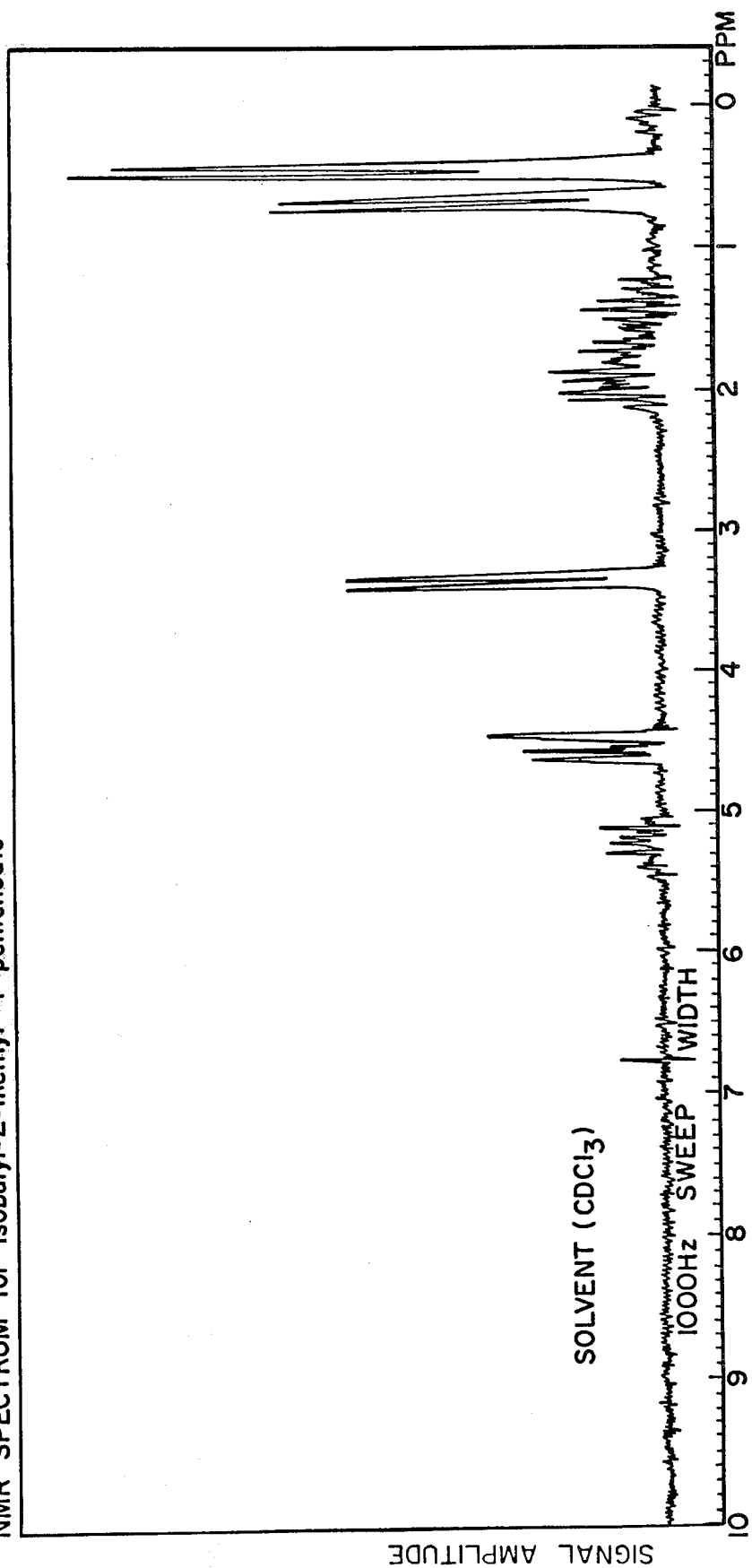

United States Patent [19]
Hall et al.

[11] 3,966,799
[45] June 29, 1976

[54] ALKYL ESTERS OF 2-METHYL-4-PENTENOIC ACID

[75] Inventors: John B. Hall, Rumson; Ching Y. Tseng, Middletown; Manfred Hugo Vock, Locust; Joaquin Vinals, Red Bank, all of N.J.; Edward J. Shuster, Brooklyn, N.Y.

[73] Assignee: International Flavors & Fragrances Inc., New York, N.Y.

[22] Filed: May 21, 1975

[21] Appl. No.: 579,567

Related U.S. Application Data

[63] Continuation-in-part of Ser. No. 490,718, July 22, 1974, Pat. No. 3,907,718.

[52] U.S. Cl. ............................ 260/486 R; 252/522; 260/526 N; 424/69; 426/650
[51] Int. Cl.² ......................................... C07C 69/52
[58] Field of Search ................................ 260/486 R

[56] References Cited
OTHER PUBLICATIONS

Shishido, K. et al., J. Am. Chem. Soc., 81, pp. 5817–5819, (1959).

*Primary Examiner*—Paul J. Killos
*Attorney, Agent, or Firm*—Arthur L. Liberman; Harold Haidt

[57] ABSTRACT

Methods are described for adding the novel compounds, isobutyl and n-hexyl esters of 2-methyl-4-pentenoic acid to foodstuffs, chewing gums or medicinal products in order to impart sweet, fruity, strawberry, pineapple-like, pear and/or green aromas and tastes.

3 Claims, 4 Drawing Figures

EXAMPLE II

NMR SPECTRUM for Isobutyl-2-methyl-4-pentenoate
SOLVENT (CDCl₃)
1000Hz SWEEP WIDTH EXAMPLE II
Isobutyl-2-methyl-4-pentenoate EXAMPLE III
n-hexyl-2-methyl-4-pentenoate NMR SPECTRUM
SOLVENT: (CDCl₃)
1000Hz SWEEP WIDTH EXAMPLE III
n-hexyl-2-methyl-4-pentenoate
INFRA RED SPECTRUM

ALKYL ESTERS OF 2-METHYL-4-PENTENOIC ACID

This application is a Continuation-in-Part of U.S. application for Letters Patent Ser. No. 490,718 filed on July 22, 1974, now U.S. Pat. 3,907,718

BACKGROUND OF THE INVENTION

The present invention relates to the novel isobutyl and n-hexyl esters of 2-methyl-4-pentenoic acid and compositions and processes using such 2-methyl-4-pentenoic acid and esters to alter the flavor of foodstuffs, chewing gums and medicinal products.

There has been considerable work performed related to substances which can be used to impart (or enhance) flavors to (or in) various types of foodstuffs, chewing gums and medicinal products. These substances are used to diminish the use of natural materials, some of which may be in short supply and to provide more uniform properties in the finished product. Sweet, fruity, strawberry, pineapple-like, pear and green aromas as well as tastes are particularly desirable for many uses in foodstuff flavors.

U.S. Pat. 3,499,769 issued on Mar. 10, 1970 discloses processes for imparting a fresh fruity flavor (particularly strawberry flavor) to foods by adding a small amount of 2-methyl-4-pentenoic acid to the foodstuff. In U.S. Pat. 3,499,769 it is emphasized that the basic nuance imparted by the 2-methyl-2-pentenoic acid is a "berry" flavor.

Quite unexpectedly, the 2-methyl-4-pentenoic acid and esters thereof of the instant invention have properties different in kind from the 2-methyl-2-pentenoic acid of U.S. Pat. 3,499,769 which is only fruity and strawberry-like and does not have the sweet, fruity, pineapple-like, pear and green aroma and taste qualities of the 2-methyl-4-pentenoic acid esters of the instant invention.

Arctander, "Perfume and Flavor Chemicals", 1969, discloses the use in perfume compositions and flavors of 4-pentenoic acid, thus:

"... only rarely used in perfume compositions mainly on fruity bases and certain artificial essential oils. It finds use in flavors on account of its sour-caramellic taste, pleasant at levels below 10 ppm, and including an almost sweet aftertaste. Higher concentrations have acrid taste and repulsively acid odor, pungent and irritating.

Traces, equivalent to 1 to 5 ppm, are used in imitation butter flavor and in various fruit flavor complexes, e.g., apple, pineapple, apricot and strawberry."

at Vol. II, No. 2452. Arctander also discloses the use of trans-2-methyl-2-butenoic acid (tiglic acid) at Vol. II, No. 2949 in perfumery:

"Spicy-rooty, sweet-sour herbaceous odor of moderate tenacity."

and the use of cis-2-methyl-2-butenoic acid (angelic acid) and alkyl esters thereof in perfumes and flavors at Vol. I, No. 238.

The alkenoic acids and esters thereof of the prior art are considered to be different in kind from the 2-methyl-4-pentenoic acid esters of the instant invention insofar as the organoleptic properties are concerned.

Rossi and Ingrosse, Chem.Abstr. 69, 95851(g) (Abstract of Gazz.Chim.Ital. 98(7), 866-83 (1968)) discloses the preparation of 2-methyl-4-pentenoic acid by reacting 3-chlor-propene-1 with 1,1-dicarboethoxyethane.

De Moura Campos and de Amarat, Chem.Abstr. 63: 4159(e) (Abstract of J.Arch.Pharm. 298(2), 92-100 (1965)) discloses the preparation of 2-methyl-4-pentenoic acid by the following reaction sequence:

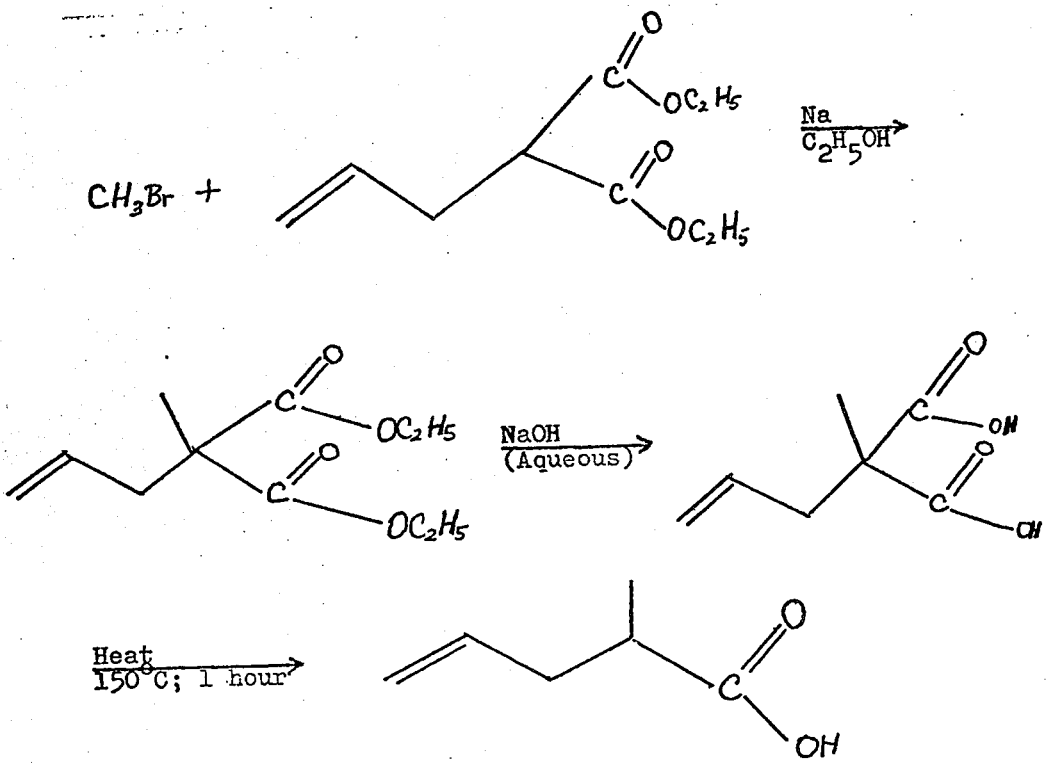

Trace and Gurante, Chem.Abstr. 55:14324(i) (Abstract of Rend.Inst.Lombardo Sci. Pt.I, Classe Sci. Mat. e Nat., 94A, 309–330 (1960) discloses a process for preparing 2-methyl-4-pentenoic acid by reacting 2-cyclopropyl-propionic acid with HBr.

Adler and Brachel Chem.Abstr. 57: 2042(d) (Abstract of Ann. 651, 141–53 (1962) sets forth a process for giving 12% yields of methyl-2-methyl-4-pentenoate by means of the following reaction:

2-methyl-4-pentenoic acid and then acidifying the salt of 2-methyl-4-pentenoic acid with acid to form 2-methyl-4-pentenoic acid itself and esterifying the 2-methyl-4-pentenoic acid with an n-hexanol or isobutanol to form an n-hexyl or isobutyl ester of 2-methyl-4-pentenoic acid or reacting the ethyl-2-methyl-4-pentenoate with an n-hexanol or isobutanol to form an n-hexyl-2-methyl-4-pentenoate or i-butyl-2-methyl-4-pentenoate.

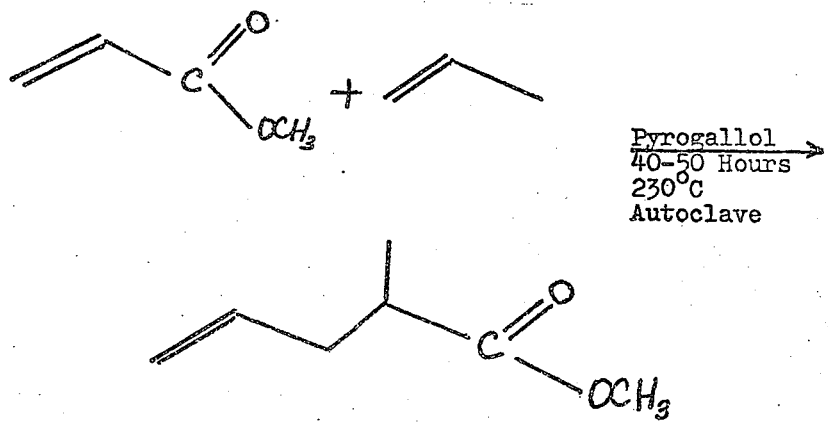

These processes as well as other processes of the prior art do not suggest the unique compounds of our invention.

THE INVENTION

It has now been discovered that solid and liquid foodstuff and flavoring compositions having sweet, fruity, strawberry, winey-cognac, pineapple-like, pear, green and apple-like aromas and tastes with cooked strawberry jam undertones be provided by the utilization of n-hexyl and isobutyl esters of 2-methyl-4-pentenoic acid having the generic formula:

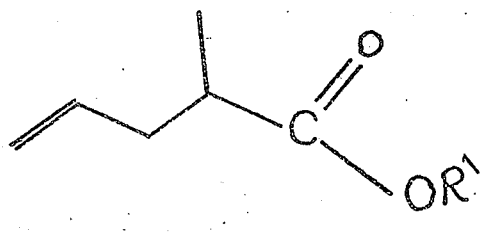

wherein R' is n-hexyl or isobutyl, in foodstuffs, chewing gums and medicinal products.

The said esters, so useful, may be produced according to the process comprising the steps of first reacting 1,1,1-triethoxy-propane with 2-propenol-1 to form ethyl-2-methyl-4-pentenoate; then saponifying the ethyl-2-methyl-4-pentenoate with base to form a salt of The 2-methyl-4-pentenoic acid isobutyl and n-hexyl esters may also be produced according to the process comprising the steps of first reacting a 1,1,1-trilower alkoxy propane with 2-propynol-1 to form an alkyl-2-methyl-3,4-pentadienoate; then, in the alternative, either (i) hydrogenating with hydrogen gas the thus-formed alkyl-2-methyl-3,4-pentadienoate in the presence of a palladium-on-carbon catalyst or a palladium-on-calcium carbonate catalyst, thereby forming a reaction mixture containing alkyl-2-methyl-4-pentenoate (isobutyl or n-hexyl ester) and using this material as such for its own organoleptic characteristics as a flavor adjuvant or enhancer or (ii) recovering the alkyl-2-methyl-4-pentenoate and using the thus-recovered material for its own organoleptic characteristics.

The 2-methyl-4-pentenoic acid n-hexyl and i-butyl esters of our invention having the generic formula:

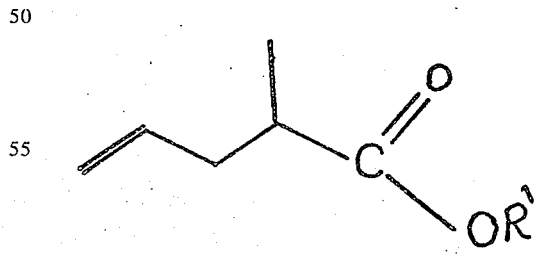

wherein R' is n-hexyl or isobutyl are intended to include singly, and in admixture the two stereoisomers of said esters, having the structures:

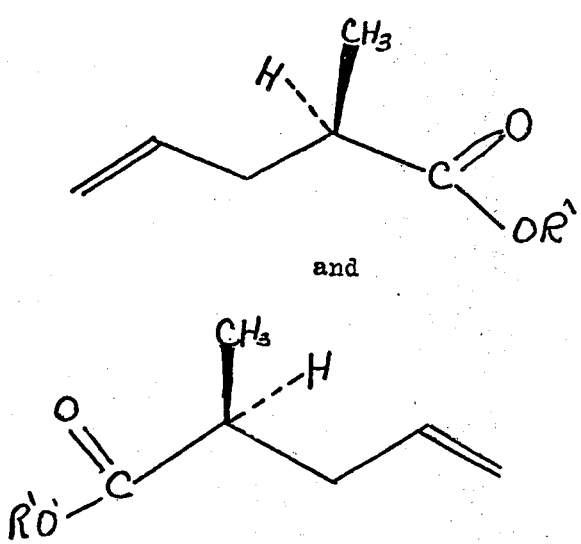

wherein R is hydrogen or $C_2$-$C_6$ lower alkyl.

One process for producing the chemical compounds useful in practicing our invention involves the steps of:

a. First reacting 1,1,1-triethoxypropane with 2-propenol-1 in the presence of a phosphoric acid catalyst to form ethyl-2-methyl-4-pentenoate. The reaction temperature range is 100°–225°C with a range of 140°–180°C being preferred. The mole ratio of reactants preferred is 1:1, with a large excess of 2-propenol-1 undesirable and a large excess of triethoxypropane being uneconomical. The reaction time is inversely dependent upon the temperature of reaction. Thus, for example, where the temperature range of reaction is 165°–185°C, the reaction time is approximately three (3) hours. The reaction product is then "worked-up" by first neutralizing the acid catalyst, the phosphoric acid, using base (e.g., sodium bicarbonate) and then fractionally distilling the reaction product.

b. The resulting ethyl-2-methyl-4-pentenoate is converted into 2-methyl-4-pentenoic acid by the standard saponification and acidification reactions. The saponification is preferably carried out using strong aqueous base, e.g., 50% aqueous sodium hydroxide or 50% aqueous potassium hydroxide admixed with methanol. After acidification of the resulting salt of 2-methyl-4-pentenoic acid (e.g., the sodium or potassium salt) using mineral acid (e.g., 6 molar aqueous hydrochloric acid) the 2-methyl-4-pentenoic acid is extracted from the aqueous phase using an organic solvent such as toluene. The organic solvent is then stripped from the acid and the acid is fractionally distilled. The resulting acid is then esterified with n-hexanol or i-butanol to form the desired ester of 2-methyl-4-pentenoic acid.

c. The ethyl-2-methyl-4-pentenoate produced as set forth in (a) supra, may be converted into the isobutyl or n-hexyl ester of 2-methyl-4-pentenoic acid, by reaction with the appropriate alkanol in the presence of a protonic acid catalyst at a temperature in the range of 100°–170°C. The preferable temperature depends upon the particular alkanol used; e.g., about 110°C in the case of isobutyl alcohol; and 140°–150°C in the case of n-hexanol. The preferred catalyst is paratoluene sulfonic acid.

The foregoing series of reactions may be illustrated as follows:

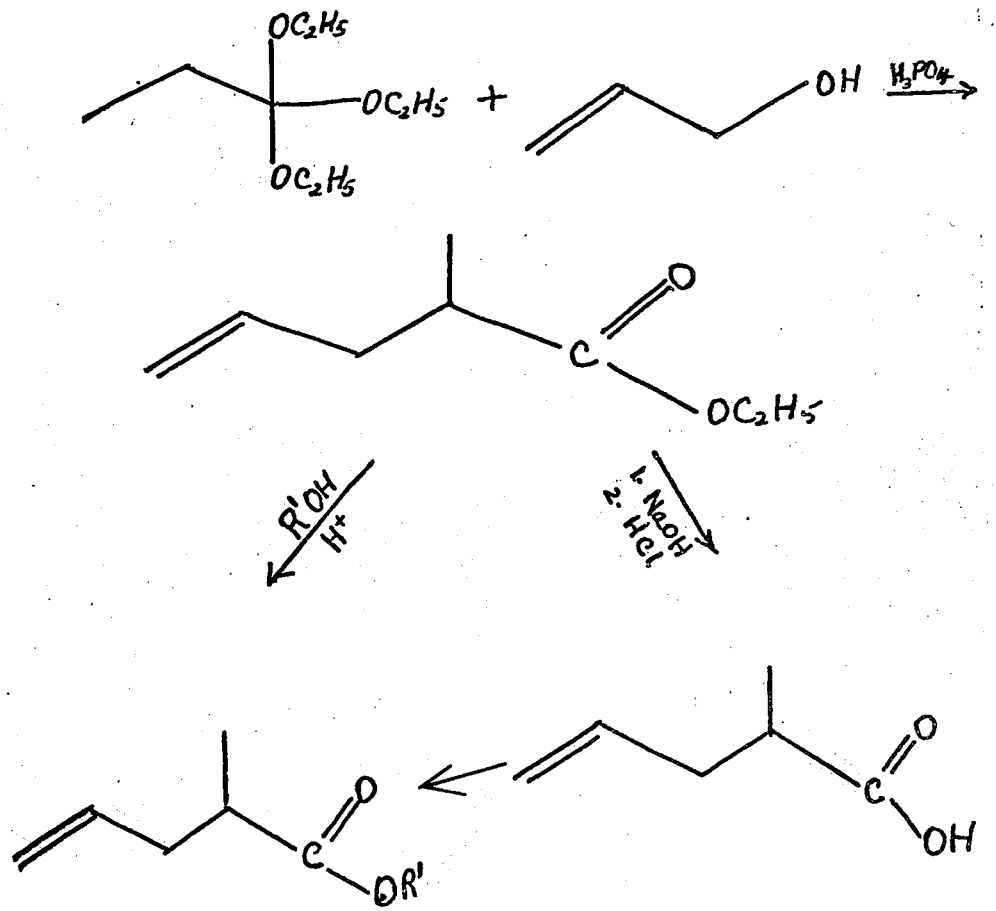

wherein R' is n-hexyl or i-butyl.

A second process for producing the chemical compounds of our invention involves the steps of:

a. First reacting a 1,1,1-trialkoxy propane (such as 1,1,1-tri-n-hexyloxy propane) with 2-propynol-1 in the presence of a propionic acid catalyst thereby forming an alkyl-2-methyl-3,4-pentadienoate. The reaction temperature range is 120°–180°C with a range of 145°–150°C being preferred. The mole ratios of reactants preferred is 1:1 with a slight excess of either reactant permissible. A large excess of 2-propynol-1 is undesirable, and a large excess of the trialkoxy propane is uneconomical. The percentage of propionic acid catalyst may vary from 1 up to 3%, but a 2% concentration of catalyst is preferred. Since the reaction temperature is in the range of 120°–180°C higher pressures of reaction are required for the carrying out of the reaction, and, accordingly, pressures of from 30 up to 100 psig are used. The reaction time is inversely dependent on the temperature of reaction. Thus, for example, where the temperature range of reaction is 150°–160°C, the reaction time is approximately 3 hours. The reaction time period varies between 2 and 6 hours, and a reaction time of 3–4 hours is preferred. The reaction product, the alkyl-2-methyl-3,4-pentadienoate, is then worked-up and this work-up operation is performed by first, if necessary, washing out the excess trialkyl orthopropionate reactant by washing with a dilute (e.g., 5%) hydrochloric acid solution. The acid is then neutralized by use of a sodium bicarbonate wash, and the reaction mass is then fractionally distilled.

b. The resulting alkyl-2-methyl-3,4-pentadienoate is then reacted with hydrogen in the presence of a palladium-on-carbon catalyst or a "Lindlar" catalyst (palladium-on-calcium carbonate). The percentage of palladium on carbon or on calcium carbonate varies from about 2% up to about 7% with a percentage of palladium-on-carbon or on calcium carbonate being preferred to be about 5%. The temperature of reaction for this hydrogenation may vary from about 10°C up to about 50°C with a preferred reaction temperature of 25°–35°C. Since the reaction is exothermic, it is usually necessary to provide external cooling to the reaction mass during the course of the reaction. The pressure of hydrogen over the reaction mass may vary from about 5 psig up to about 50 psig, with the most preferred pressure being 20 psig. It has been found that pressures above 20 psig give rise to larger amounts of undesired side products. The hydrogenation reaction may be carried out in the presence of or in the absence of a solvent. When a solvent is used, it is required that it be an inert (non-reactive) solvent such as isopropyl alcohol, hexane or ethanol, with the alkyl moiety of the alcohol solvent being the same as the alkyl moiety of the alkoxy group of the ester being hydrogenated. If a solvent is used, it is preferred that the mole ratio of solvent:pentadienoate ester be approximately 1:1. The percentate of catalyst in the reaction mass may vary from 0.125% up to about 2.0% with a percentage of catalyst of about 0.25% being preferred. When using a Lindlar catalyst, the hydrogenation reaction produces a mixture of alkyl-2-methyl-cis-3-pentenoate and alkyl-2-methyl-4-pentenoate in the ratio of from about 6:4 up to about 7:3. As a result, the desired alkyl-2-methyl-4-pentenoate for use in the instant invention may, if desired, be enriched with respect to the alkyl-2-methyl-cis-3-pentenoate by means of fractional distillation or the mixture resulting may be used as such for its organoleptic properties as a flavor adjuvant or enhancer for use in foodstuffs, medicinal products or chewing gum. Where the catalyst used is palladium-on-carbon rather than a Lindlar catalyst (palladium on-calcium carbonate), a mixture of alkyl-2-methyl-cis-3-pentenoate, alkyl-2-methyl-4-pentenoate and alkyl-2-methyl-pentanoate is formed which may be used as such for its organoleptic properties as a flavor adjuvant or enhancer for foodstuffs, chewing gum and medicinal products or which may be separated as by means of fractional distillation. In any event, at the end of the hydrogenation reaction, the reaction mass is filtered in order to separate catalyst from liquid phase desired product, and the filtrate is distilled using a fractional distillation column operated under vacuum.

c. If desired, the resulting alkyl-2-methyl-4-pentenoate and other esters which have not been separated therefrom after the hydrogenation reaction may be converted into 2-methyl-4-pentenoic acid and other acids by means of standard saponification and acidification reactions. The saponification is preferably carried out using strong aqueous base, e.g., 50% aqueous sodium hydroxide or 50% aqueous potassium hydroxide admixed with methanol. After acidification of the resulting salt of 2-methyl-4-pentenoic acid (e.g., the sodium or potassium salt) using mineral acid, the 2-methyl-4-pentenoic acid is extracted from the aqueous phase using an organic solvent such as diethyl ether. The organic solvent is then stripped from the acid, and the acid is fractionally distilled. The resulting acid may be used as such or it may, if desired, be esterified with isobutanol or n-hexanol to form the n-hexyl or isobutyl ester of 2-methyl-4-pentenoic acid.

d. The mixture of esters including the alkyl-2-methyl-4-pentenoate ester produced as set forth in (b) supra, may be converted into other esters such as the n-hexyl ester of 2-methyl-4-pentenoic acid by reaction with n-hexanol in the presence of a protonic acid catalyst at a temperature in the range of 100°–170°C. The preferred temperature depends upon the particular alkanol used; e.g., about 110°C in the case of isobutyl alcohol; and 140°–150°C in the case of n-hexanol. The preferred catalyst is paratoluene sulfonic acid.

The foregoing series of reactions may be illustrated as follows:

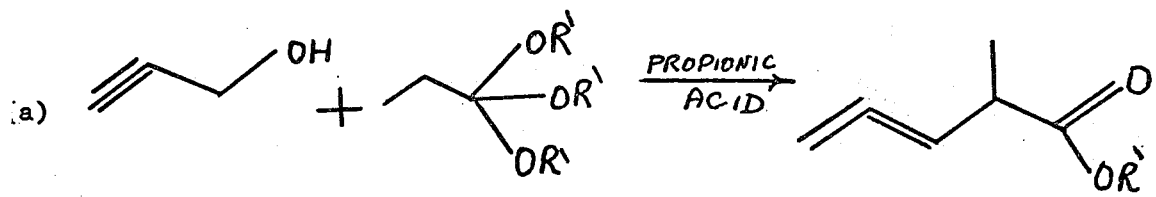

(b) 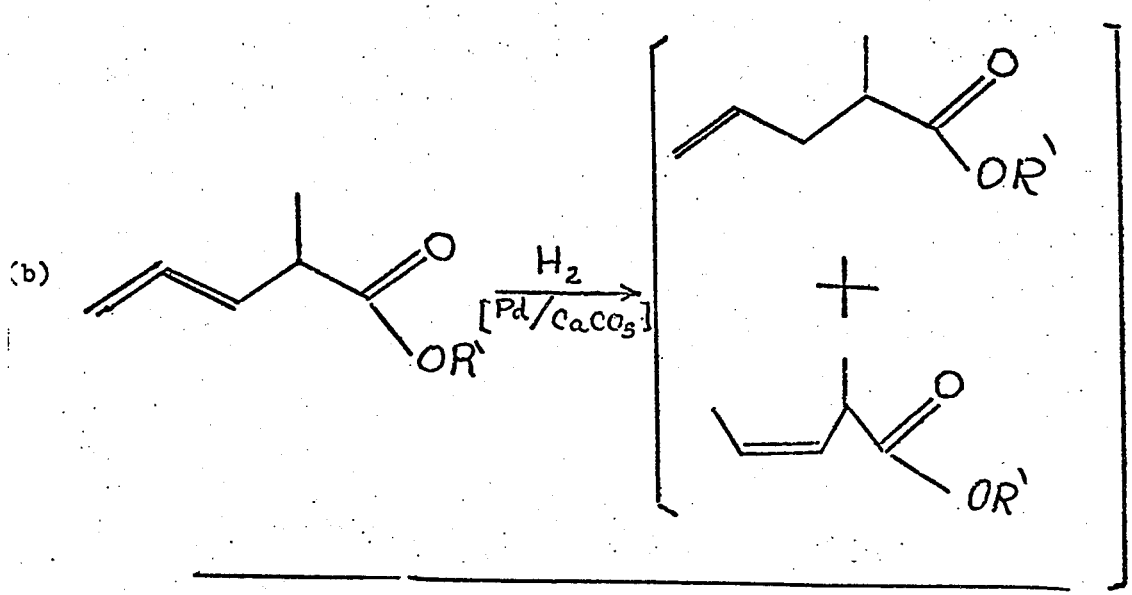

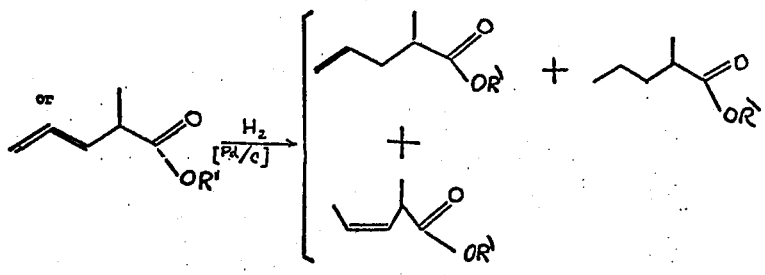

wherein R' is n-hexyl and isobutyl.

Examples of specific reaction products, the uses of which are contemplated within the scope of our invention, and their respective organoleptic properties are set forth in the following table:

| Compound | Flavor Properties |
| --- | --- |
| Isobutyl-2-methyl-4-pentenoate | At 5 ppm, fruity, pineapple and strawberry aroma and fruity, pineapple, strawberry and sweet taste. |
| n-Hexyl-2-methyl-4-pentenoate | At 5 ppm, pear and green aroma and taste notes. |

When the 2-methyl-4-pentenoic acid isobutyl or n-hexyl esters of our invention are used as flavor adjuvants for altering the flavor of foodstuffs, medicinal products and chewing gums, the nature of the co-ingredients included with the said-2-methyl-4-pentenoic acid ester in formulating the product composition will also serve to alter the organoleptic characteristics of the ultimate foodstuff, medicinal product or chewing gum treated therewith.

As used herein in regard to flavors, the term "alter" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

As used herein, the term "foodstuff" includes both solids and liquids ingestible materials which usually do, but need not, have nutritional value. Thus, foodstuffs include soaps, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin, chewable medicinal tablets and toothpaste.

The term "chewing gum" is intended to mean a composition which comprises a substantially water-insoluble, chewable plastic gum base such as chicle, or substitutes therefore, including jelutong guttakay, rubber or certain comestible natural or synthetic resins or waxes. Incorporated with the gum base in admixture therewith may be plasticizers or softening agents, e.g., glycerine; and a flavoring composition which incorporates the alkyl-2-methyl-4-pentenoate of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates, starches pectins, and emulsifiers, e.g., mono-and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane.

The specific flavoring adjuvant selected for use may be either solid or liquid depending upon the desired physical form of the ultimate product, i.e., foodstuff, chewing gum or medicinal product, whether simulated or natural, and should, in any event, be capable of providing an environment in which the 2-methyl-4-pentenoic acid ester can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of 2-methyl-4-pentenoic acid ester employed in a particular instance can vary over a relatively wide range whereby to its desired organoleptic effects having reference to the nature of the product are achieved. Thus, correspondingly, greater amounts would be necessary in those instances wherein the ultimate food composition or chewing gum or medicinal product to be flavored is relatively bland to the taste, whereas relatively minor quantities may suffice for purposes of enhancing the composition merely deficient in natural flavor or aroma. The primary requirement is that the amount selected to be effective, i.e., sufficient to alter the organoleptic characteristics of the parent composition, whether foodstuff per se or flavoring composition.

The use of insufficient quantities of 2-methyl-4-pentenoic acid ester will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions and medicinal products, it is found that quantities of 2-methyl-4-pentenoic acid alkyl ester ranging from a small but effective amount, e.g., 0.03 parts per million up to about 20 parts per million by weight based on total composition are suitable. Concentrations in excess of the maximum quantity stated are not normally recommended since they fail to prove commensurate enhancement of organoleptic properties. In those instances wherein the 2-methyl-4-pentenoic acid alkyl ester is added to the foodstuff as an integral component of a flavoring composition, it is, of course, essential that the total quantity of flavoring composition employed be sufficient to yield an effective 2-methyl-4-pentenoic acid alkyl ester concentration in the food-stuff product.

Food flavoring compositions, chewing gum flavoring compositions and medicinal product flavoring compositions prepared in accordance with the present invention preferably contain the 2-methyl-4-pentenoic acid alkyl ester in concentrations ranging from about 0.25% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 2-methyl-4-pentenoic acid alkyl ester with, for example, gum arabic gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar, and the like and 2-methyl-4-pentenoic acid alkyl ester in a dry blender until the requisite degree of uniformity is achieved.

It is presently preferred to combine with the 2-methyl-4-pentenoic acid alkyl ester the following adjuvants:
p-Hydroxybenzylacetone;
Geraniol;
Maltol;
Ethyl methyl phenyl glycidate;
Benzyl acetate;
Vanillin;
Methyl cinnamate;
Ethyl pelargonate;
Methyl anthranilate;
Isoamyl acetate;
Alpha ionone;
Ethyl butyrate;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene)

The following examples are given to illustrate embodiments of the invention as it is presently preferred to practice it. It will be understood that these examples are illustrative, and the invention is not to be considered as restricted thereto except as indicated in the appended claims. All parts and percentages given herein are by weight unless otherwise specified.

EXAMPLE I

PREPARATION OF ETHYL-2-METHYL-4-PENTENOATE

To a two liter autoclave, the following materials are added:

| | |
|---|---|
| Triethyl orthopropionate | 495. g |
| (1,1,1-triethoxypropane) | (2.4 moles) |
| Allyl alcohol | 140. g |
| | (2.4 moles) |
| Phosphoric acid (85%) | 12. g |

The autoclave is sealed and the mixture is heated with stirring at 165°–185°C for a period of three hours.

The autoclave is then opened and 12.6 g sodium bicarbonate is added to the reaction mass in order to neutralize the phosphoric acid. 30 g Primol (a registered trademark for mineral oil manufactured by the Exxon Co. of Linden, N.J.) is then added as a still base, and the reaction mass is fractionally distilled on a 1 × 20 inches packed Goodloe distillation column (i) at atmospheric pressure and 129°C (yielding a mixture of ethanol and ethyl propionate (245 g) and (ii) at 40 mm Hg. pressure and 75°C (yielding 264 g of ethyl-2-methyl-4-pentenoate. Yield, based on triethyl orthopropionate used, 73.5%.

Mass spectral analysis: m/e = 69, 41, 29, 27 39 and 68.

| NHR Analysis | Interpretation | |
|---|---|---|
| 1.16 ppm (d) | $CH_3-\overset{H}{\underset{\underset{O}{\|}}{C}}-\overset{}{\underset{\|}{C}}-$ | 6H |
| 1.20 (t) | $CH_3-CH_2-O-\underset{\underset{O}{\|}}{C}-$ | |
| 2.64–2.08 (m) | $=C-CH_2 + HC-$ <br> $\underset{\underset{O}{\|}}{}$ | 3H |
| 4.12 (q) | $Me-CH_2-O-\underset{\underset{O}{\|}}{C}-$ | 2H |
| 5.18–4.98 (m) | $HC=CH_2$ | 2H |
| 5.98–5.56 (m) | $HC=CH_2$ | 1H |
| IR Analysis | | |
| 915 cm⁻¹ | | |
| 1015 | | |
| 1090 | | |
| 1140 | | |
| 1175 | | |
| 1225 | | |
| 1240 | | |
| 1380 | | |
| 1460 | | |
| 1730 | | |
| 2940 | | |
| 2980 | | |

EXAMPLE II

PREPARATION OF ISOBUTYL-2-METHYL-4-PENTENOATE

Into a 500 ml reaction vessel equipped with stirrer, 3 inches splash column and thermometer, the following materials are added:

| | |
|---|---|
| Ethyl-2-methyl-4-pentenoate (Produced according to Example I) | 56. g (0.4 moles) |
| Isobutyl Alcohol | 112. g |
| p-Toluene sulfonic acid | 0.5 g |
| Primol | 10. g |
| Ionol (A registered trademark for butylated hydroxytoluene manufactured by the Shell Chemical Company) | 0.1g |

The reaction mass is heated to 110°C and atmospheric temperature for a period of 10 hours, while distilling off light fractions (head temperature: 45°–83°C). After the ten-hour period, 72.4 g light fractions are distilled.

Vacuum is then applied and the remaining unreacted isobutyl alcohol is distilled. The residual product is then rushed over yielding a mixture of isobutyl-2-methyl-4-pentenoate and ethyl-2-methyl-4-pentenoate. This mixture is refractioned through a 12 plate Vigreaux column at 95°–96°C and 40 mm Hg pressure yielding isobutyl-2-methyl-4-pentenoate.

The nuclear magnetic resonance analysis is as follows:

| ppm | Interpretation | |
|---|---|---|
| 0.91 ppm (d) | $CH_3-\overset{\underset{\|}{CH_3}}{\underset{\|}{C}}-$ | 6H |
| 1.14 ppm (d) | $CH_3-\overset{\|}{\underset{\|}{C}}-$ | 3H |
| 1.92 ppm (m) | $\overset{CH_3}{\underset{\|}{HC-}}$ $=C-CH_2-$ $+ HC-\overset{O}{\underset{\|}{C}}-$ | 1H |
| 2.60–2.1 ppm (m) | $-CH_2-O-\overset{O}{\underset{\|}{C}}-$ | 3H |
| 3.82 ppm (d) | | 2H |
| 5.1–4.94 $\Big\}AB_2$ | $-C=CH_2$ | 2H |
| 5.94–5.54 | $HC=C-$ | 1H |

The infra-red analysis is as follows:

| | |
|---|---|
| 920 cm⁻¹ | 1460 |
| 990 | 1470 |
| 1140 | 1730 |
| 1180 | 2940 |
| 1380 | 2960 |

Figure 2:
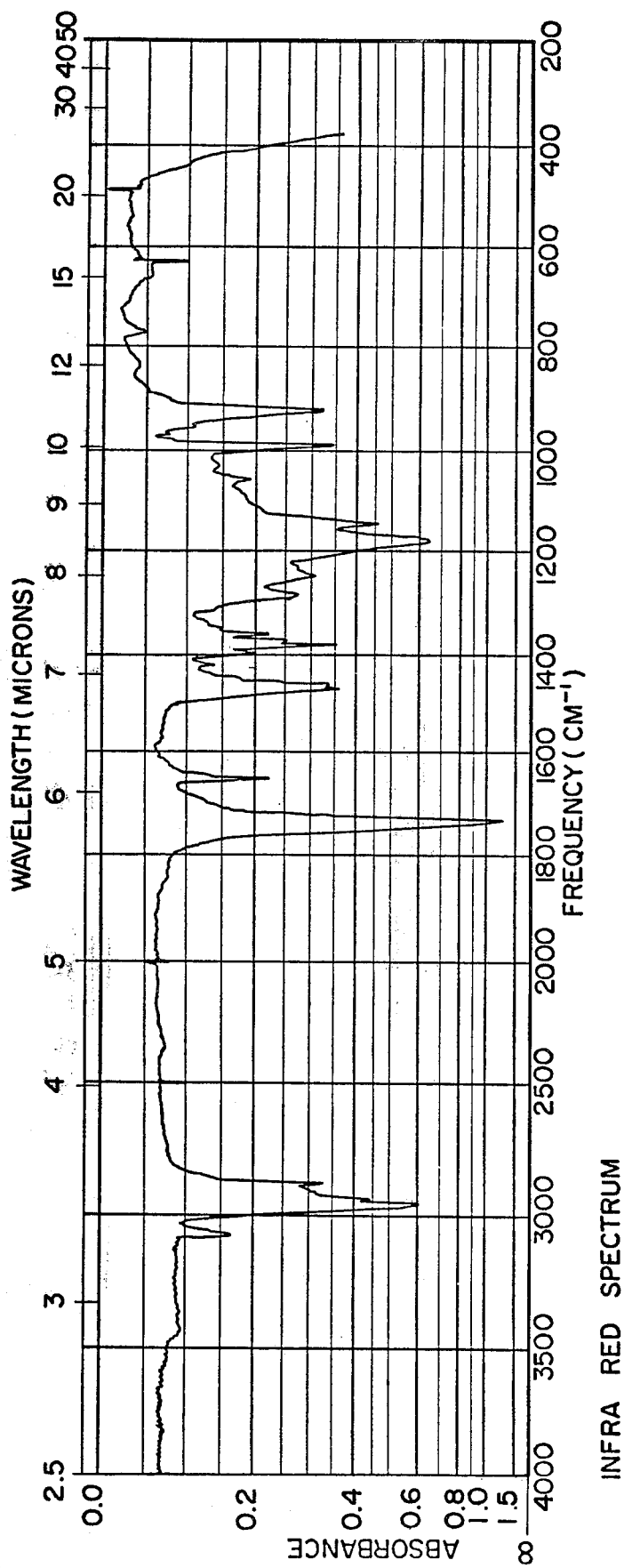

Mass spectral data: Parent peak, then in decreasing order of intensity:
m/e= 170/69, 41, 57, 27, 97
The NMR spectrum is set forth in FIG. 1.
The IR spectrum is set forth in FIG. 2.

EXAMPLE III

PREPARATION OF n-HEXYL-2-methyl-4-PENTENOATE

Into a 250 ml reaction vessel equipped with stirrer, 3 inches splash column and thermometer, the following materials are added:

| | |
|---|---|
| Ethyl-3-methyl-4-pentenoate (Prepared according to Example I) | 56. g (0.4 moles) |
| n-Hexyl Alcohol | 60. g |
| p-Toluene Sulfonic Acid | 0.4 g |
| Primol | 10. g |
| Ionol | 0.1 g |

The reaction mass is heated to 140°–150°C at atmospheric pressure over a period of 18 hours, while distilling off light fractions. By the end of the 18-hour period, 11.7 g of low boilers is distilled. The residual product is then rushed over, and then fractionated on a 12 plate Vigreaux column at 88°C and 3.9–4.1 mm Hg. pressure to yield the n-hexyl-2-methyl-4-pentenoate.

The nuclear magnetic resonance analysis is as follows:

| ppm | Interpretation | |
|---|---|---|
| 0.88 ppm (t) | $C\underline{H}_3-(CH_2)-$ | 3H |
| 1.14 ppm (d) 1.70–1.12 ppm (m) | $CH_3-\overset{H}{\underset{\|}{C}}-$ $-CH_2-$ $=C-CH_2- +$ | 3H 8H |
| 2.58–2.04 ppm (m) | $H\overset{\|}{\underset{\|}{C}}-\overset{O}{\underset{\|}{C}}-$ | 3H |
| 4.04 ppm (t) | $-C\underline{H}_2-CH_2-O-\overset{O}{\underset{\|}{C}}-$ | 2H |
| 5.10–4.94 $\Big\}AB_2$ | $HC=C\underline{H}_2$ | 2H |
| 5.94–5.54 | $\underline{H}C=CH_2-$ | 1H |

The infra-red analysis is as follows:

| | | |
|---|---|---|
| 910 cm⁻¹ | 1460 | 2980 |
| 980 | 1730 | |
| 1140 | 2850 | |
| 1180 | 2930 | |

Figure 3:
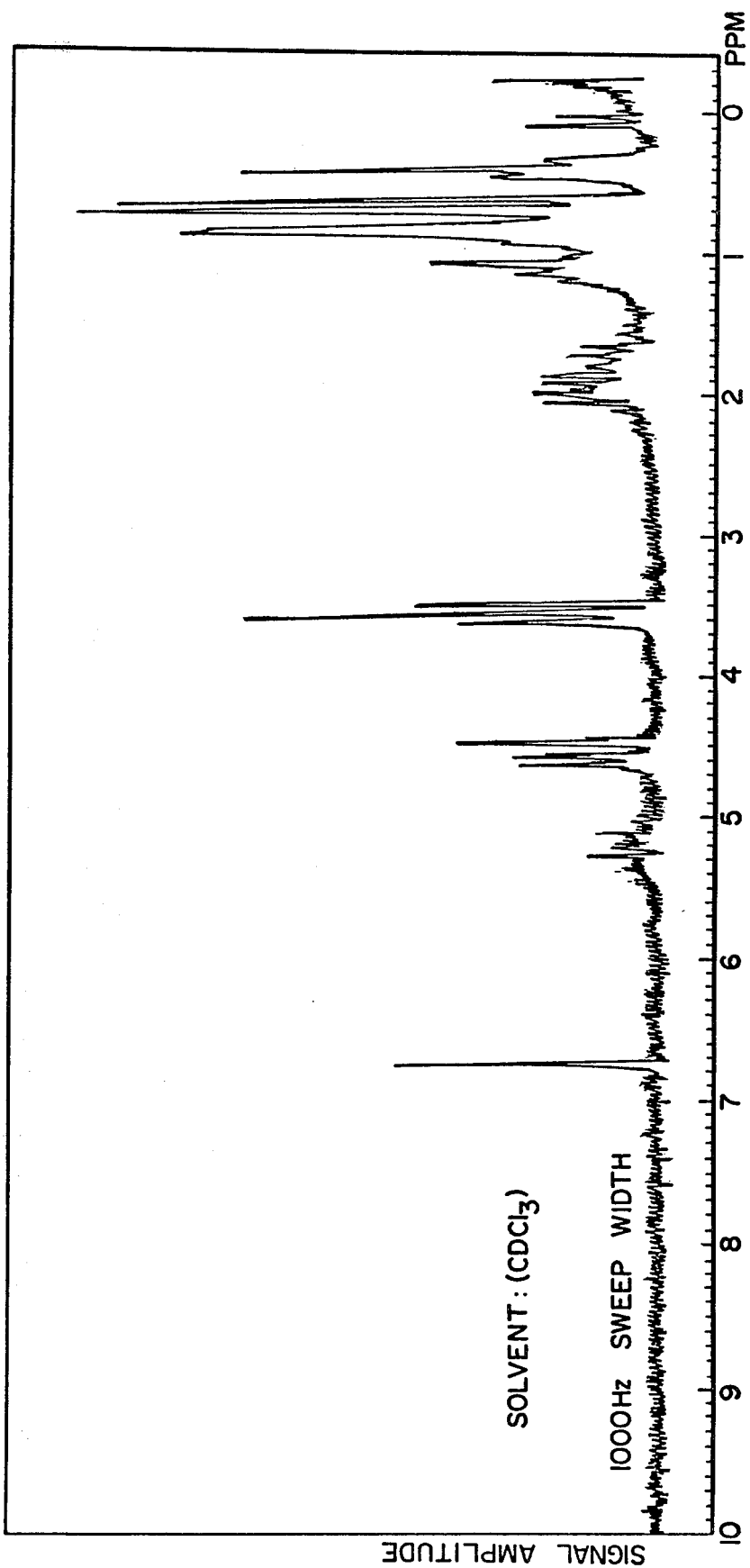
Figure 4:
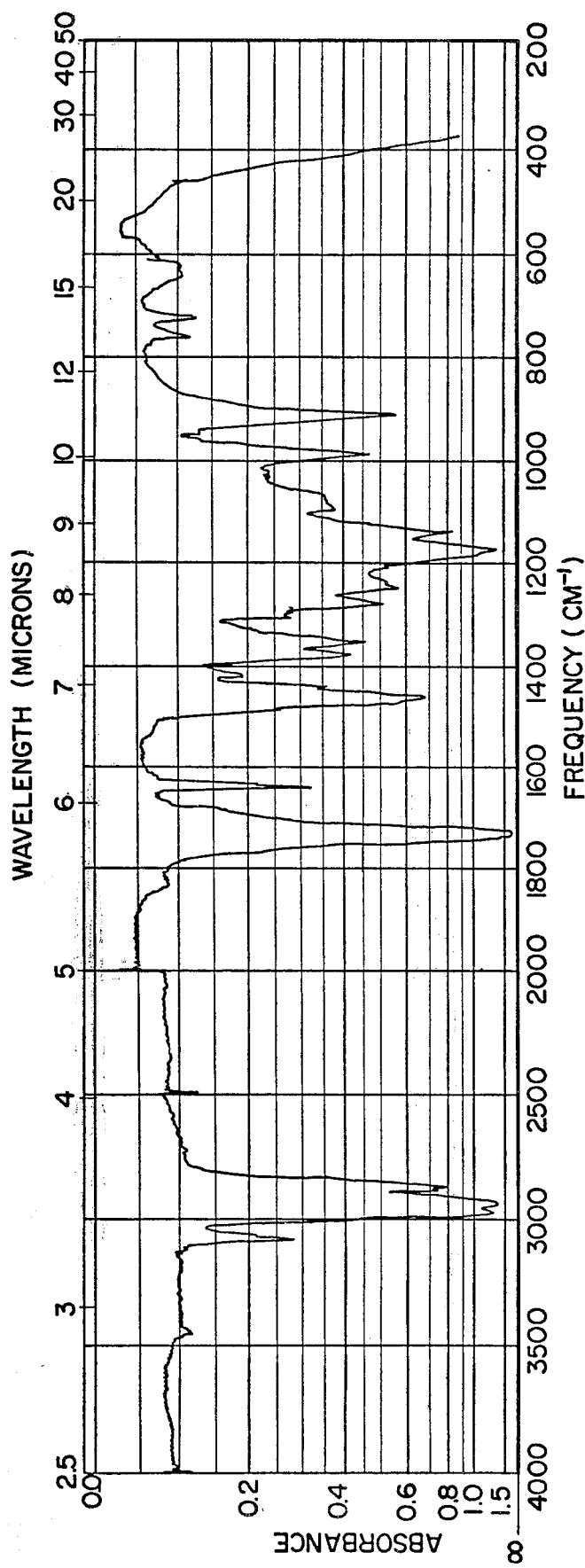

Mass spectral data: Parent peak, then in decreasing order of intensity:
m/e= 198/69, 41, 43, 27, 114, 29
The NMR spectrum is set forth in FIG. 3.
The IR spectrum is set forth in FIG. 4.

EXAMPLE IV

The following concentrate is prepared:

| Ingredient | Percent |
|---|---|
| Geraniol | 1.00 |
| Ethyl methyl phenyl glycidate | 3.50 |
| Isobutyl-2-methyl-4-pentenoate (Prepared according to the process of Example II) | 5.00 |
| Vanillin | 5.50 |
| Ethyl pelargonate | 13.00 |
| Isoamyl acetate | 14.00 |
| Ethyl butyrate | 58.00 |
| | 100.00 |

EXAMPLE V

Another concentrate is prepared as follows:

| Ingredient | Percent |
| --- | --- |
| Naphthyl ethyl ether | 1.0 |
| Vanillin | 2.5 |
| Ethyl methyl phenyl glycidate | 3.0 |
| Isobutyl-2-methyl-4-pentenoate (Prepared according to the process of Example II) | 5.0 |
| Ethyl acetate | 9.5 |
| Isoamyl acetate | 12.0 |
| Ethyl butyrate | 26.0 |
| Isoamyl butyrate | 41.0 |
| | 100.00 |

EXAMPLE VI

The concentrate prepared in Example VI is dissolved in 4 volumes of propylene glycol and the mixture is added to a hard candy melt at the rate of 1.5 oz. of the concentrate solution per 100 lbs. of melt. After the finished candy has been produced, it is found to have an excellent strawberry flavor. When the candy is compared with candy made under the same conditions, but without the isobutyl-2-methyl-4-pentenoate prepared according to the process of Example III in the concentrate, it is found to have an inferior strawberry flavor.

EXAMPLE VII

The propylene glycol solution of the concentrate as prepared in Example VI is added to a simple syrup at the rate of 1/8 oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the isobutyl-2-methyl-4-pentenoate prepared according to the process of Example V.

EXAMPLE VIII

The flavor concentrate prepared in Example V is admixed with gum arabic and in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the isobutyl-2-methyl-4-pentenoate prepared according to the process of Example II in the concentrate.

EXAMPLE IX

PEAR FLAVOR FORMULATION

The following mixture is prepared:

| Ingredient | Parts by Weight |
| --- | --- |
| Vanillin | 2.0 |
| Ethyl Hexanoate | 0.5 |
| Ethyl Decanoate | 1.0 |
| Benzyl Acetate | 0.5 |
| Ethyl Octanoate | 2.0 |
| Gamma Undecalactone (10% in 95% food grade ethyl alcohol) | 2.0 |
| Alpha Ionone (0.1% in 95% food grade ethanol) | 5.0 |
| Hexyl Acetate | 25.0 |
| Lemon Oil, cold pressed | 5.0 |
| Ethyl Butyrate | 7.0 |
| Ethyl Acetate | 40.0 |
| Butyl Acetate | 20.0 |
| Amyl Valerate | 65.0 |
| Amyl Acetate | 640.0 |
| Ethyl Alcohol | 185.0 | n-Hexyl-2-methyl-4-pentenoate prepared according to the process of Example III is added to a first portion of the basic pear formulation at the rate of 5%. Another portion of the basic pear formulation is used "as-is". Both flavor formulations are compared in water at a level of 50 ppm. Both flavors are evaluated by a bench panel of five members. The pear flavor with the addition of the n-hexyl-2-methyl-4-pentenoate is judged by the bench panel as having the notes of the ripe, fresh, Bartlet pear, and is thus preferred against the flavor without the said n-hexyl-2-methyl-4-pentenoate.

What is claimed is:

1. A compound having the structure

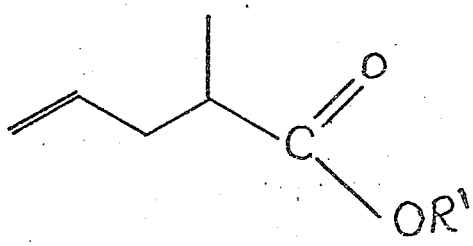

wherein R' is selected from the group consisting of n-hexyl and i-butyl.

2. The compound of claim 1 wherein R' is n-hexyl.
3. The compound of claim 1 wherein R' is i-butyl.

* * * * *